United States Patent [19]

Concannon

[11] 4,425,331

[45] Jan. 10, 1984

[54] BIOLOGICAL CONTROL

[76] Inventor: Joseph N. Concannon, 107 Briarcliff Dr., East Norwich, N.Y. 11732

[21] Appl. No.: 311,008

[22] Filed: Oct. 13, 1981

[51] Int. Cl.³ .................. A01N 63/00; C12N 1/20
[52] U.S. Cl. .................... 424/93; 435/253; 435/859
[58] Field of Search .............. 435/253, 859; 424/93

[56] References Cited

U.S. PATENT DOCUMENTS 3,911,110 10/1975 Smirnoff ............................ 424/93
4,223,007 9/1980 Spence et al. ..................... 424/93

*Primary Examiner*—David M. Naff
*Assistant Examiner*—Frederick W. Pepper
*Attorney, Agent, or Firm*—Scully, Scott, Murphy & Presser

[57] ABSTRACT

A biologically pure culture of the microorganism *Micrococcus pseudoflaccidifex*, ATCC No. 31970, which is capable of producing death in insects by mechanisms associated with wilt disease.

12 Claims, No Drawings

BIOLOGICAL CONTROL

BACKGROUND OF THE INVENTION

The present invention relates to a method of controlling insect populations, especially those which are herbivorous in nature, and in particular, to a method for effecting such control through biological means.

Over the years the existence of different species of insects which affect their local environment during one or more stages of their life cycles have at times had a harmful or deleterious influence on the local vegetation and/or indigenous creatures. Such environmental impact has many times proven harmful to the physical, economic, and social well being of humans. In recent times, examples of undesirable insects include the Gypsy Moth[1], which essentially denudes broadleaf trees, and the Mediterranean Fruit Fly, which infests and destroys crops of fruit intended for human consumption.

[1] See Marshall, E., *Science*, Vol. 213, dated Aug. 28, 1981, pp. 991-993.

Whether insects are directly detrimental to humans, such as those mentioned above, or merely locally upset the balance of nature, a definite need exists for control of insect populations or insects. Early control methods were primarily chemical in nature. More recent controls have been chemical and biological. Various methods were adopted for use against insects during vulnerable phases of insect life cycle, including toxic chemicals, introduction of sterile specimens into insect populations, the use of lures such as pheromones to attract insects, etc. Disease causing organisms, e.g., *Bacillus thuringiensis*, have also been used with some measure of success.

Which of the foregoing methods of control may be used will vary depending on the type of insect involved as well as the environment in which they are to be used. Unfortunately, the use of chemical agents for insect control has certain drawbacks such as unintended residual effect, indiscriminate lethality to living organisms, unpredictable long term effects on recipient organisms, persistence in food chains, and public disapproval of the use of chemical agents.

Consequently, it has become a desirable alternative to effect control of insect population through biological means. One method for such control is by seeding an insect population of a particular species with sterile male insects so that mating instincts are satisfied without the production of offspring. This method also has certain drawbacks in that it lacks immediacy and that it may not be sufficiently extensive in the face of a huge insect population.

Many of the problems associated with control of insect populations, such as selectivity, existence of residuum, lack of immediacy, etc., appear to be solved by the present invention which, in sum, induces the death of insects by a mechanism or mechanisms associated with wilt disease.

Wilt disease or "flackerie" in an insect is characterized by cessation of eating and sluggishness in activity, followed by complete motionlessness. After a period of time, usually several hours, dark putrified liquid oozes from body orifices such as the mouth and anus. The insect, e.g., caterpillar, becomes extremely flaccid, the legs losing their grip until finally, with only one or two of its false feet or with its anal claspers it hangs limp and dead. Its skin, which is by the time of death usually black, may be easily ruptured to emit a dark, thin liquid having an extremely offensive odor.

While wilt disease is best known as affecting the gypsy moth larva, *Lymantria dispar Linnaeus*, at least 35 other species of insects have been reported to be affected by the same or very similar diseases. See Stienhaus, *Insect Microbiology: An Account of the Microbes Associated with Insects & Ticks*, page 414 (1946). At first it was believed that a small, motile coccus, *Gyrococcus flaccidifex*, was the etiologic agent of the disease in the gypsy moth, however, extensive study in the area of gypsy moth wilt disease performed by R. W. Glaser and J. W. Chapman early in this century, led to a determination that wilt disease in the gypsy moth is caused by a filterable virus. The efficacy of this work is evident from the fact that the term "wilt disease" came to be used as a general term to designate any virus-caused disease of insects, id. at 421.

Further study regarding wilt disease led to the discovery of another micrococcus, i.e., *Micrococcus flaccidifex danai*, Index No. 3322-22120-2131, which has been identified as a causative agent of "wilt" disease in the Monarch Butterfly caterpillar, *Danais plexippus*; see *American Museum Novitiates*, No. 251, pages 5 and 6 (1927).

While these and possibly other etiological investigations into insect death by wilt disease have revealed different, lethal microorganisms, it is not believed that any wilt disease-inducing microorganism has been effectively used as a biological control of insect population.

SUMMARY OF THE INVENTION

It has now been discovered by me that the microorganism *Micrococcus pseudoflaccidifex*, ATCC No. 31970, is very effective in producing death in insects, generally in the larvae stages. By insect is meant insects per se and mites. Specifically, this bacterium is capable of producing death in those insects which ingest the organism. Ostensibly, the target insect population is controlled by inducing death in such insects by mechanism(s) associated with wilt disease. It is suggested that such mechanisms might be any one of, or combination of, gut penetration, tissue digest, inactivation of immune mechanisms, etc., but no recommendation is set forth herein which might in any way limit the scope of the present invention.

*Micrococcus pseudoflaccidifex* was discovered by me as a causative agent of wilt disease in the Monarch Butterfly. The organism was isolated by standard microbiological procedures from dead larvae in a laboratory population. Testing to date indicates that *Micrococcus pseudoflaccidifex* also produces death in the Gypsy Moth caterpillar, Silk Worms, Tobacco Horn Worm, and other insects upon ingestion of the microorganism. It is not intended to in any way limit the scope of the present invention by the extent of test results currently available.

Since death is induced by the microorganism upon mere ingestion thereof by the larvae, population control is easily effected by deposition of *M. pseudoflaccidifex* in the environs of the object insect population in a form that makes it available for consumption by the larvae of said insect(s). For instance, a concentration of the lethal micrococcus can be suspended in an environmentally safe medium and then sprayed or fogged or applied to ingestible material by any feasible method in an area to be treated. It is also contemplated that an effective population of the bacteria may be lyophilized for ultimate use by a consumer. While this is one convenient way to effect insect population control by use of the present invention, it is in no way intended to limit the scope of the present invention by this suggested method.

For a better understanding of the present invention, together with other and further objects, reference is made to the following description, taken in conjunction with the accompanying examples.

DETAILED DESCRIPTION OF THE INVENTION

In accordance with the present invention, a microbiologically pure culture of the microorganism *Micrococcus pseudoflaccidifex*, ATCC No. 31970, is provided which produces death in insects. The above-named organism, which is a micrococcus, was isolated from the bodies of Monarch Butterfly caterpillars obtained from Queens, N.Y. Specimens of the Monarch Butterfly were retrieved in the form of eggs and nurtured in a colony separated from the natural environment.

Observation of the butterflies in the larvae stage revealed reduced activity level in several specimens followed by death ostensibly caused by wilt disease. Upon opening the bodies of the dead caterpillers, a thin, dark putrid fluid was emitted, it having been observed that essentially all of the inside organs of the caterpillar had been destroyed.

In an effort to determine the cause of death, the body fluid was streaked out on culture plates and eventually a pure culture of the microorganism was isolated by conventional pour plate technique and investigated.

The organism was fed to, and inoculated into, Monarch caterpillars. All insects died and the organism was reisolated from the treated caterpillars.

THE MICROORGANISM

*Micrococcus pseudoflaccidifex*, ATCC No. 31970, has the following morphological characterisics. It is a gram positive micrococcus. This staining may vary depending on the age of the culture. It grows aerobically on agar or in broth media generally in groups of two, although at times they may appear as short rods with four or more cells in a chain. The colonies are circular, smooth, and of glistening off-white appearance.

While the organism will grow to an adequate extent on a variety of media, it has thus far been best cultured on Brain Heart Infusion (BHI) Broth or agar supplemented with inactivated horse serum in the ratio of 0.5 ml. to 10 ml. of media.

The carbohydrate metabolism of *M. pseudoflaccidifex* is as follows (1% phenol red sugar):

| Gram Stain | *M. pseudoflaccidifex* Positive | *M. flaccidifex danai* Negative |
|---|---|---|
| Fermentation: | | |
| Arabinose | Acid only | Acid and Gas |
| Sucrose | Acid only | Acid and Gas |
| Inulin | Acid only | Acid and Gas |
| Mannose | Acid only | Acid and Gas |
| Colonies | Round | Crenate Margin |

The method used for determining carbohydrate metabolism utilized standard procedures such as those described by A. C. Baird-Parker, "Methods for Identifying Staphylocci and Micrococci," in the 1979 edition of *Identification Methods for Microbiologists* published by the Society of Applied Microbiologists, edited by F. A. Skinner and D. W. Lavelock which is incorporated by reference herein, and the test procedures of Gunn, et al., "Comparison of Methods for Identifying Staphylococcus and Micrococcus," *Journal of Chemical Microbiology*, Vol. 14, No. 2, August 1981, pages 195-200 which is also incorporated by reference herein.

Further biochemical reactions were also conducted in accordance with procedures outlined in the above referenced publications with the following results:

Biochemical Metabolism of *Micrococcus Pseudoflaccidifex*

- Aerobic and Microaerophilic
- Hemolysis: Alpha
- Catalase: Positive
- Gelatin Stab: Saccate liquefaction, while pellicle and sediment
- Litmus Milk: Casein Hydrolysis slow—48 hrs.
- $H_2S$: Negative
- Capsule: In Brain Heart Infusion (BHI) medium
- Indole: Negative
- Deoxycholate: Positive after seven days
- Nitrate Reduction: Positive
- Themostabile Nuclease: Positive
- Growth in 10% NaCl: Negative
- Solubility in Bile: Soluble
- Erythromycin: Sensitive
- Lysostaphin: Sensitive
- Lysozyme: Resistant
- Novobiocin: Resistant In order to distinguish *Micrococcus pseudoflaccidifex* from *Microccus flaccidifex danai*, as described by F. Martin Brown[2], the following physiological comparison has been made.

[2]See Brown, *Descriptions of New Bacteria Found in Insects*, American Museum Novitiates, No. 251, Feb. 2, 1927, page 5.

| Carbohydrate | Acid Growth |
|---|---|
| Arabinose | Acid formation |
| Fructose | Acid formation |
| Galactose | Acid formation |
| Maltose | Acid formation |
| Starch | Acid formation |
| Sucrose | Acid formation |
| Inulin | Slight Acid formation |
| Lactose | Slight Acid formation |
| Mannose | Slight Acid formation |
| Sorbitol | Slight Acid formation |
| Xylose | Slight Acid formation |

THE EFFECT OF THE MICROORGANISM

In tests performed to determine the effectiveness of the microorganism on different types of larvae, the larvae were subjected to doses of *M. pseudoflaccidifex* first by inoculation. For example, Silk Worms were inoculated with the organism in numbers from over a thousand to just 40 and all died with wilt disease. (The number 40 was found a convenient minimum because of difficulties with obtaining such low quantities of the microorganism). Similarly, inoculation of Monarch caterpillars, Gypsy Moth caterpillars and Tobacco Horn Worms resulted in 100% death.

In tests performed to determine lethality of the bacteria, 24 hour cultures were painted on leaves and the bacteria were ingested by the four different species of caterpillars. All died with wilt disease.

In an experiment with Gypsy Moth caterpillars, within two days 76% were dead and in three days 100% were dead. Control caterpillars showed approximately a 4–5% death in three days, thus confirming an at least 95% death rate from the bacteria.

It is thus contemplated that *Micrococcus pseudoflaccidifex* will also be effective in all insects, especially herbivorous insects in the larvae stage, even at a very low concentration. Presently this bacterium is not known to cause disease in humans or in non-insect animals. Accordingly, the present invention includes a method for controlling the population of all insects and in particular for controlling herbivorous insects.

While there has been described what is presently believed to be the preferred embodiment of the invention, those skilled in the art will realize that changes and modifications may be made thereto without departing from the spirit of the invention, and it is intended to claim all such changes and modifications as fall within the true scope of the invention.

I claim:

1. A biologically pure culture of the microorganism *Micrococcus pseudoflaccidifex*, ATCC No. 31970.

2. A composition useful for controlling insect population which comprises a biologically pure culture of the microorganism *Micrococcus pseudoflaccidifex* ATCC 31970 in an environmentally safe medium wherein said *Micrococcus pseudoflaccidifex* is initially present in a concentration sufficient to cause disease in insects.

3. A method of causing disease in an insect which comprises introducing a biologically pure culture of the microorganism *Micrococcus pseudoflaccidifex* into said insect in a concentration sufficient to cause disease.

4. The method of claim 3 wherein said insects are herbivorous.

5. The method of claim 3 wherein the disease is wilt disease.

6. The method of claim 3 wherein said insect is in the larvae stage.

7. The method of claim 3 wherein said insect is selected from the group consisting of Monarch Butterfly capterpillar, Gypsy Moth caterpillar, Silk Worm, and Tobacco Horn Worm.

8. The method of claim 3 wherein said form of introducing said microorganism is by applying an environmentally safe medium containing said microorganism on or in an ingestible material in the environment in which it is desired to cause disease in the insect.

9. The method of claim 8 wherein said medium is water-based.

10. The method of claim 8 wherein the concentration of microorganism in the medium is about 1 part per million by weight.

11. The composition of claim 2 wherein said concentration is at least about 1 part per million by weight.

12. The composition of claim 2 wherein said concentration is at least about 40 per insect.

* * * * *

UNITED STATES PATENT OFFICE
CERTIFICATE OF CORRECTION

PATENT NO. : 4,425,331  Page 1 of 2
DATED : 01/10/84
INVENTOR(S) : Joseph M. Concannon It is certified that error appears in the above-identified patent and that said Letters Patent are hereby corrected as shown below:

At Col. 3, Line 53-61, the chart

| Gram Stain | M. pseudoflaccidifex<br>Positive | M. flaccidifex danai<br>Negative |
|---|---|---|
| Fermentation: | | |
| Arabinose | Acid only | Acid and Gas |
| Sucrose | Acid only | Acid and Gas |
| Inulin | Acid only | Acid and Gas |
| Mannose | Acid only | Acid and Gas |
| Colonies | Round | Crenate Margin | should read:

| Carbohydrate | Acid Growth |
|---|---|
| Arabinose | Acid formation |
| Fructose | Acid formation |
| Galactose | Acid formation |
| Maltose | Acid formation |
| Starch | Acid formation |
| Sucrose | Acid formation |
| Inulin | Slight Acid formation |
| Lactose | Slight Acid formation |
| Mannose | Slight Acid formation |
| Sorbitol | Slight Acid formation |
| Xylose | Slight Acid formation |

UNITED STATES PATENT AND TRADEMARK OFFICE
CERTIFICATE OF CORRECTION

PATENT NO. : 4,425,331

DATED : 01/10/84

INVENTOR(S) : Joseph N. Concannon

Page 2 of 2

It is certified that error appears in the above-identified patent and that said Letters Patent is hereby corrected as shown below:

Col. 4, line 36-47, the chart

| Carbohydrate | Acid Growth |
|---|---|
| Arabinose | Acid formation |
| Fructose | Acid formation |
| Galactose | Acid formation |
| Maltose | Acid formation |
| Starch | Acid formation |
| Sucrose | Acid formation |
| Inulin | Slight Acid formation |
| Lactose | Slight Acid formation |
| Mannose | Slight Acid formation |
| Sorbitol | Slight Acid formation |
| Xylose | Slight Acid formation | should read:

| | *M. pseudoflaccidifex* | *M. fluccidifex donai* |
|---|---|---|
| Gram Stain | Positive | Negative |
| Fermentation: | | |
| Arabinose | Acid only | Acid and Gas |
| Sucrose | Acid only | Acid and Gas |
| Inulin | Acid only | Acid and Gas |
| Mannose | Acid only | Acid and Gas |
| Colonies | Round | Crenate Margin |

Signed and Sealed this

Tenth Day of April 1984

[SEAL]

*Attest:*

*Attesting Officer*

GERALD J. MOSSINGHOFF

*Commissioner of Patents and Trademarks*

UNITED STATES PATENT AND TRADEMARK OFFICE
CERTIFICATE OF CORRECTION

PATENT NO. : 4,425,331
DATED : 01/10/84
INVENTOR(S) : CONCANNON, JOSEPH N.

It is certified that error appears in the above-identified patent and that said Letters Patent are hereby corrected as shown below:

At Column 4, line 15, "while pellicle" should read: --white pellicle--.

Signed and Sealed this

Twenty-ninth Day of May 1984

[SEAL]

Attest:

GERALD J. MOSSINGHOFF

Attesting Officer

Commissioner of Patents and Trademarks